(12) United States Patent
    Spira

(10) Patent No.: US 11,191,839 B2
(45) Date of Patent: Dec. 7, 2021

(54) COMPOSITION FOR TREATMENT OF INFERTILITY IN A FEMALE SUBJECT

(71) Applicant: ISIFER AB, Danderyd (SE)

(72) Inventor: Jack Spira, Tyresö (SE)

(73) Assignee: ISIFER AB, Danderyd (SE)

( * ) Notice: Subject to any disclaimer, the term of this patent is extended or adjusted under 35 U.S.C. 154(b) by 0 days.

(21) Appl. No.: 15/769,813

(22) PCT Filed: Oct. 11, 2016

(86) PCT No.: PCT/SE2016/000055
    § 371 (c)(1),
    (2) Date: Apr. 20, 2018

(87) PCT Pub. No.: WO2017/069672
    PCT Pub. Date: Apr. 27, 2017

(65) Prior Publication Data
    US 2019/0240338 A1    Aug. 8, 2019

(30) Foreign Application Priority Data
    Oct. 23, 2015  (SE) .................................... 1500425-2

(51) Int. Cl.
    | | |
    |---|---|
    | *A61K 47/42* | (2017.01) |
    | *A61K 9/08* | (2006.01) |
    | *A61K 31/167* | (2006.01) |
    | *A61K 9/00* | (2006.01) |
    | *A61K 47/36* | (2006.01) |
    | *A61K 47/38* | (2006.01) |
    | *A61P 15/08* | (2006.01) |
    | *A61K 47/34* | (2017.01) |
    | *A61K 9/16* | (2006.01) |
    | *A61K 9/48* | (2006.01) |
    | *A61K 9/50* | (2006.01) |
    | *A61K 47/02* | (2006.01) |
    | *A61K 47/12* | (2006.01) |
    | *A61K 47/18* | (2017.01) |
    | *A61K 47/26* | (2006.01) |
    | *A61M 5/178* | (2006.01) |
    | *A61M 35/00* | (2006.01) |
    | *A61K 9/06* | (2006.01) |
    | *A61M 25/00* | (2006.01) |

(52) U.S. Cl.
    CPC ............ *A61K 47/42* (2013.01); *A61K 9/0014* (2013.01); *A61K 9/0019* (2013.01); *A61K 9/0095* (2013.01); *A61K 9/08* (2013.01); *A61K 9/1611* (2013.01); *A61K 9/1617* (2013.01); *A61K 9/1623* (2013.01); *A61K 9/1652* (2013.01); *A61K 9/485* (2013.01); *A61K 9/4858* (2013.01); *A61K 9/4866* (2013.01); *A61K 9/5031* (2013.01); *A61K 31/167* (2013.01); *A61K 47/02* (2013.01); *A61K 47/12* (2013.01); *A61K 47/183* (2013.01); *A61K 47/26* (2013.01); *A61K 47/34* (2013.01); *A61K 47/36* (2013.01); *A61K 47/38* (2013.01); *A61M 5/178* (2013.01); *A61M 35/00* (2013.01); *A61P 15/08* (2018.01); *A61K 9/06* (2013.01); *A61M 25/00* (2013.01); *A61M 2205/04* (2013.01); *A61M 2210/04* (2013.01); *A61M 2210/1017* (2013.01); *A61M 2210/1021* (2013.01); *A61M 2210/1425* (2013.01)

(58) Field of Classification Search
    CPC .. A61K 9/0014; A61K 9/0019; A61K 9/0095; A61K 9/08; A61K 9/1611; A61K 9/1617; A61K 9/1623; A61K 9/1652; A61K 9/485; A61K 9/4858; A61K 9/4866; A61K 9/5031; A61K 9/06; A61K 31/167; A61K 47/02; A61K 47/12; A61K 47/183; A61K 47/26; A61K 47/34; A61K 47/36; A61K 47/38; A61K 47/42; A61M 5/178; A61M 35/00; A61M 25/00; A61M 2205/04; A61M 2210/04; A61M 2210/1017; A61M 2210/1021; A61M 2210/1425
    See application file for complete search history.

(56) References Cited

U.S. PATENT DOCUMENTS

| | | | | |
|---|---|---|---|---|
| 5,977,143 | A | * 11/1999 | Edelstam | ............. A61K 31/445 514/330 |
| 2002/0042132 | A1* | 4/2002 | Gardner | ............... C12N 5/0604 435/388 |
| 2011/0280763 | A1* | 11/2011 | Trokel | ................... A61K 31/37 422/24 |

FOREIGN PATENT DOCUMENTS

| | | |
|---|---|---|
| WO | 96/34599 A1 | 11/1996 |
| WO | 98/35676 A1 | 8/1998 |
| WO | WO 98/35676 | * 8/1998 |

(Continued)

OTHER PUBLICATIONS

Bungum et al. Recombinant human albumin as protein source in culture media used for IVF in Reproductive BioMedicine (Feb. 2002 article), 2002.*

(Continued)

*Primary Examiner* — Blessing M Fubara
(74) *Attorney, Agent, or Firm* — Porter Wright Morris & Arthur LLP

(57) ABSTRACT

A pharmaceutical composition for treating infertility in a female subject substantially consists of local anesthetic of amide type such as lidocaine, human albumin, viscosity controlling agent selected from recombinant hyaluronic acid and combination of recombinant hyaluronic acid and water-soluble cellulose ether, optionally citrate, glucose, and/or amino acid, water optionally comprising one or more ions selected from the group consisting of sodium, potassium, magnesium, calcium, acetate, chloride, sulfate. Also disclosed is a method of treating infertility by administration of the composition to a female subject in need thereof.

29 Claims, No Drawings

(56) References Cited

FOREIGN PATENT DOCUMENTS

| WO | 99/01114 A1 | | 1/1999 |
|---|---|---|---|
| WO | 00/53183 A1 | | 9/2000 |
| WO | WO 00/53183 | * | 9/2000 |
| WO | 03/029447 A1 | | 4/2003 |
| WO | 2011/145993 A1 | | 11/2011 |

OTHER PUBLICATIONS

Edelstam, Greta et. al., A new rapid and effective method for treatment of unexplained infertility, Human Reproduction, vol. 23, Issue 4, pp. 852-856 (2008).

Morad, Ahmed Walid A., Prospective randomized study for hydrotubation with or without lidocaine before intrauterine insemination in unexplained infertility, Middle East Fertility Society Journal, 17:250-255 (2012).

Wickstrom K., Pertubation with lignocaine as a new treatment of dysmenorrhea due to endometriosis: a randomized controlled trial, Human Reproduction, vol. 27, No. 3, p. 695-701 (Jan. 9, 2012).

Johnson N. et. al., Tubal flushing for subfertility (Review), Cochrane Database of Systematic Reviews, I18(2):CD003718 (2005).

* cited by examiner

COMPOSITION FOR TREATMENT OF INFERTILITY IN A FEMALE SUBJECT

FIELD OF THE INVENTION

The present invention relates to a pharmaceutical composition for treatment of infertility, such as endometriosis related infertility and unexplained infertility. The present invention also relates to a method of treatment by use of the composition and to a method for its preparation.

BACKGROUND OF THE INVENTION

There are many biological causes of infertility. For example, infertility may be caused by aberrant hormone levels or dysfunctional ovulation in the female, or of dysfunctional sperm production in the male. A large number of couples are however diagnosed as having unexplained infertility. Artificial insemination is often tried as first treatment for couples with unexplained infertility, while the couples are on the waiting list for in vitro fertilization (IVF). Pertubation, i.e. flushing of the fallopian tubes, has been shown to increase the chances of achieving pregnancy for couples with unexplained infertility and infertility in patients diagnosed with early endometriosis (Johnson et al. (2005), *Cochrane Database Syst Rev*, 18(2): CD003718).

Endometriosis is a gynecologic disease characterized by the presence of tissue which is histologically identical to endometrium, i.e. the membrane lining the inside of the mammalian uterus, outside the uterine cavity. Endometriosis is associated with infertility and in many women with unexplained infertility endometriosis may be the underlying cause.

Lidocaine (also called lignocaine) is a well-known local anaesthetic of the chemical formula

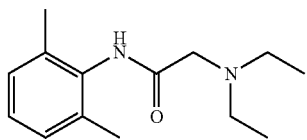 [SMILES: CCN(CC)CC(=O)Nc1c(C)cccc1C]

It is known to have membrane stabilizing, anti-arrhythmic and anti-inflammatory properties. In this application, the term "lidocaine" comprises pharmaceutically acceptable salts thereof, such as the hydrochloride, in which form it is preferably administered. Lidocaine has membrane stabilizing, anti-arrhythmic and anti-inflammatory properties. Pertubation (tubal flushing) with low doses of lidocaine before artificial insemination has been shown to increase pregnancy rates in couples with unexplained infertility (Edelstam, G. et al. (2008), *Human Reproduction*, Vol. 23, No. 4, pp. 852-856).

US 2002/00421132 A1 discloses an aqueous supplement and culture media useful for culturing mammalian gametes and embryonic tissue comprising one or more of human albumin, fermented hyaluronic acid and citrate.

Hyaluronic acid, also known as hyaluronan, is a naturally occurring polymer of repeated disaccharide units of N-acetylglucosamine and D-glucuronic acid. It is widely distributed throughout the body, where it contributes to cell proliferation and migration. It is also a component of the group A streptococcal extracellular capsule. Hyaluronic acid has been found useful in a variety of medical applications.

There is a need for pharmaceutical compositions and/or methods for efficient treatment of infertility, such as endometriosis related infertility.

OBJECTS OF THE INVENTION

An object of the invention is to provide a pharmaceutical composition, which enhances fertility and which can be used for treatment of infertility, such as infertility of unknown origin or infertility in a patient diagnosed with endometriosis.

Additional objects of the invention are to provide a method for treating infertility of unknown origin and a method for treating infertility in a patient diagnosed with endometriosis, by administering the composition of the aforementioned kind to a person in need thereof.

Further objects of the invention will become apparent from the following summary of the invention, the description of preferred embodiments thereof, and the appended claims.

SUMMARY OF THE INVENTION

The various aspects of the present invention are fully disclosed in the appended claims.

According to the present invention is disclosed a composition for treating infertility, such as infertility in a patient diagnosed with endometriosis, and for treating female infertility of unknown origin. The composition of the invention is injectable or implantable into the abdominopelvic cavity, in particular injectable by a hypodermic syringe through the cervix via the fallopian tubes, also known as perturbation.

In one aspect the present invention provides a pharmaceutical composition comprising or consisting of a local anesthetic of the amide type or a pharmaceutically acceptable salt thereof selected from the group consisting of articaine, bupivacaine, cinchocaine, etidocaine, levobupivacaine, lidocaine, mepivacaine, oxetacine, prilocaine, ropivacaine, tolycaine, and trimecaine, human albumin and hyaluronic acid, and optionally citrate, glucose and/or amino acid(s), in an aqueous media, in particular water, or in powderous form for reconstitution with an aqueous media, in particular with water. It is preferred for human albumin or hyaluronic acid or both to be of recombinant origin. Pharmaceutically acceptable salts include but are not limited to hydrochloride, hydrobromide, and sulphate. Lidocaine, in particular in form of its hydrochloride, is a preferred local anesthetic of the invention. Another preferred local anesthetic of the invention is prilocaine.

The pharmaceutical composition of the invention is more efficient than previously known compositions comprising an aqueous solution of lidocaine or lidocaine hydrochloride and inorganic and/or organic salt for osmotic pressure control, such as Ringer's solution comprising sodium chloride. The pharmaceutical composition of the present invention provides a higher fertility rate than known lidocaine compositions of the aforementioned kind.

A preferred concentration of the local anesthetic of the invention, such as of lidocaine or lidocaine hydrochloride, in the pharmaceutical composition of the invention is from 0.1 mg/ml to 2.5 mg/ml, more preferred from 0.3 mg/ml to 1.5 mg/ml, most preferred about 1.0 mg/ml.

For preparing the composition of the invention the local anesthetic of the invention, in particular lidocaine or lidocaine hydrochloride, is dry or wet mixed, in no particular order, with human albumin and hyaluronic acid, and optionally citrate, glucose and/or amino acid(s).

The human albumin of the present invention is preferably of recombinant origin. In the pharmaceutical composition of the present invention recombinant human albumin offers a number of advantages over naturally occurring human serum albumin (HSA). By using recombinant human albumin instead of plasma/blood derived HSA the potential risk of contaminating the pharmaceutical composition with blood derived constituents or contagious particles is eliminated. Moreover, the recombinant protein is less variable than protein isolated from a biological source such as blood. Pharmaceutical compositions comprising recombinant human albumin are thus easier to standardize. The production of recombinant human albumin is well known in the art. In one embodiment the recombinant human albumin is obtained from genetically modified yeast, engineered to express human albumin protein.

A preferred concentration of human albumin in the pharmaceutical composition of the invention is from 0.1 mg/ml to 20.0 mg/ml, more preferred from 0.5 mg/ml to 10.0 mg/ml.

According to a preferred aspect of the invention the pharmaceutical composition comprises a viscosity controlling agent. The viscosity controlling agent of the invention is one lacking pharmacological effect in respect of the condition to be treated. Furthermore, the viscosity controlling agent of the invention is preferably biodegradable.

A preferred viscosity controlling agent of the invention is hyaluronic acid, which term includes pharmaceutically acceptable salts thereof such as sodium, potassium, magnesium or calcium salts. Most preferred are sodium salts of hyaluronic acid. Hyaluronic acid is a mucopolysaccharide of high molecular weight.

The hyaluronic acid of the present invention is preferably of recombinant origin. As with recombinant human albumin the use of recombinant hyaluronic acid enables standardization and provides greater safety and stability of the pharmaceutical composition.

US 2002/0042132 A1 discloses that citrate does enhance the properties of recombinant human albumin. For the present invention any citrate that is known in the art for use in pharmaceutical compositions and/or culture media may be used. Examples of useful citrate include sodium citrate, calcium citrate, citric acid, and combinations thereof. Preferably sodium citrate is used. A preferred concentration of, optional, citrate in the pharmaceutical composition of the invention is from 0.1 mM/L to 5.0 mM/L, more preferred from 0.1 mM/L to 1.0 mM/L.

According to a further aspect of the invention the composition comprises glucose. In the composition glucose controls osmotic pressure and constitutes a source of energy. The glucose content is preferably up to about 5% by weight. If the composition is desired to be isosmotic with serum the content of glucose is selected correspondingly, taking into account the contribution of other components to the osmotic pressure.

According to the method of the invention the composition is administered locally to the tissue in need thereof rather than systemically.

For preparing the composition of the invention the local anesthetic of the amide type, in particular lidocaine or a pharmaceutically acceptable salt thereof, and the other components are dissolved in water.

In one embodiment the pharmaceutical composition of the present invention is free from non-recombinant macromolecules or macromolecules of animal or human origin.

Another embodiment the pharmaceutical composition of the present invention comprises a viscosity controlling agent in addition to hyaluronic acid for adjusting the viscosity of the composition. A pharmaceutical composition of higher viscosity has the advantage of providing prolonged exposure of the pharmaceutical composition to the tissue being treated, compared to a pharmaceutical composition of lower viscosity. Any pharmaceutically acceptable viscosity regulating agent known in the art may be used. In a preferred embodiment the viscosity regulating agent is cellulose ether, in particular hydroxypropyl-methyl cellulose (HPMC).

The viscosity of the pharmaceutical composition is preferably adjusted to from 40 cp (centipoise) to 600 cp, more preferred from 100 cp to 400 cp. When hyaluronic acid is used as the sole viscosity regulating agent in the pharmaceutical composition of the invention, a preferred concentration of hyaluronic acid is from 0.02 mg/ml to 2 mg/ml or 3 mg/ml or 5 mg/ml, more preferred from 0.1 mg/ml to 1 mg/ml or from 0.2 mg/ml to 0.8 mg/ml. When hyaluronic acid is used in combination with a cellulose ether, in particular HPMC, as viscosity controlling agent, its concentration as well as the concentration of the cellulose ether is adapted to provide the composition with the aforementioned preferred viscosity.

In another aspect the present invention provides a method for treating infertility in a person, comprising providing a pharmaceutical composition according to the invention and administering an amount thereof to said person, in particular abdominopelvically or intraperitoneally. Preferred is intraperitoneal administration via the fallopian tubes. Administration via the fallopian tubes may, for instance, be by pertubation, as described in Edelstam, G. et al. (2008), *Human Reproduction*, Vol. 23, No. 4, pp. 852-856; Wickström, K. et al. (2012), *Human Reproduction*, Vol. 27, No. 3, pp. 695-701). The amount of composition administered is from about 1 ml to about 40 ml, more preferably from 2 ml to 25 ml. The person to be treated may for example have been diagnosed with unexplained infertility or with endometriosis.

Intraperitoneal administration may, for instance, be by injection of the composition of the invention into the peritoneal cavity by means of a syringe, by infusion into the peritoneal cavity by means of a catheter, by surgical deposition in the abdominal cavity, by transdermal absorption via the abdominal wall or by subcutaneous deposition. Sustained or delayed release preparations known in the art comprising the pharmaceutical composition of the invention can be implanted by surgery in the abdominal cavity or injected into it, such as in form of microparticles comprising the composition or comprising the composition except for its water component, or they can be deposited subcutaneously in the abdomen. Transdermal absorption can be achieved by, for instance, a transdermal cotton pad covered with the composition of the invention. The viscosity of the composition of the invention for use with the pad may exceptionally be substantially higher than 600 cp, such as 1000 or 2000 cp or even higher.

The composition is preferably administered to the peritoneal cavity in a volume of from 5-10 ml to 20-40 ml, in particular of about 10 or 20 ml.

The invention will now be described in greater detail by reference to a number of preferred examples thereof.

DETAILED DESCRIPTION OF THE INVENTION

Materials

A stock solution of 0.5 mg/ml lidocaine in Ringer acetate was made as follows: NaCl (8.5 g), KCl (0.3 g), $CaCl_2 \cdot H_2O$ (0.33 g) and Lidocaine (0.5 g) were dissolved in 800 ml injection grade water (WFI). The pH was adjusted to 7.0 with NaOH and water added to 1000 ml.

A stock solution of 1.0 mg/ml lidocaine in Ringer acetate was made as follows: NaCl (8.6 g), KCl (0.3 g), $CaCl_2 \cdot H_2O$ (0.33) g and lidocaine (1.0 g) were dissolved in 800 ml of WFI. The pH was adjusted to 7.0 with NaOH and water added to 1000 ml. A hyaluronic acid stock solution (gel) was prepared containing 40 mg/ml hyaluronic acid in WFI.

EXAMPLE 1

Aqueous solutions containing 1 mg/ml hyaluronic acid were prepared by mixing 0.1 ml of hyaluronic acid stock solution with 3.9 ml of either 0.5 mg/ml lidocaine or 1.0 mg/ml lidocaine stock solutions (above) in a glass vial. Solutions were mixed by extensive swirling at room temperature. After swirling for 30 min the hyaluronic acid stock solution (gel) had not been dissolved completely in the lidocaine solutions but was still present as a gel.

EXAMPLE 2

The procedure of Example 1 was repeated at 37° C. with a negative result since hyaluronic acid gel was seen to adhere to the glass of the vial. The same experiments performed with plastic vials provided similar results.

EXAMPLE 3

3.9 ml of the two stock solutions were pipetted into a glass vial and heated to about 40° C. To the solution was added 0.1 ml of 40 mg/ml hyaluronic acid to make a solution of 1 mg/ml of hyaluronic acid. Care was observed not to have the hyaluronic acid sticking to the glass. The vials were vigorously swirled for two min. Inspection of the vials showed that the hyaluronic acid had dissolved completely.

EXAMPLE 4

Stock solutions containing 0.5 mg/ml lidocaine or 1.0 mg/ml lidocaine were prepared and heated to about 40° C. To each of the vials was added the amount of hyaluronic acid listed in Table 1. Care was taken not touch the wall of vials when adding the hyaluronic acid. After swirling for about 5 minutes the gel in all vials had dissolved. An aqueous solution containing 16 mg/ml of lidocaine was like a soft jelly and proved difficult to press through a hypodermic syringe. At a concentration of 8 mg/ml the solution was viscous but easy to handle and press through a hypodermic syringe of same gauge. The osmolarity of the solutions was tested by using a Fiske Model 210 Micro Osmometer.

TABLE 1

Fluid consistency of hyaluronic acid-containing pertubation solutions

| Pertubation solutions prepared from stock solutions A and B | | | | |
|---|---|---|---|---|
| A. Hyaluronic acid 40 mg/ml | 0.2 parts | 0.4 parts | 0.8 parts | 1.6 parts |
| B. Lidocaine 0.5 mg/ml | 3.8 parts | 3.6 parts | 3.2 parts | 2.4 parts |
| Final concentration of hyaluronic acid (mg/ml) | | | | |
| | 2 | 4 | 8 | 16 |
| Fluid viscosity | Liquid | Slightly viscous | Viscous | Gel-like |
| Osmolarity (mOsm/kg) | Not tested | 265 | 246 | Not tested |

EXAMPLE 5

Hyaluronic acid was exchanged for hydroxypropyl-methyl cellulose (HPMC) as a viscosity controlling agent. It was noted that HPMC is also possible to use to control viscosity but a larger volume is needed. A stock solution of 5% HPMC in WFI was prepared.

TABLE 2

Fluid consistency of hydroxypropyl methyl cellulose-containing pertubation solutions

| Pertubation solutions prepared from stock solutions C and D | | | | |
|---|---|---|---|---|
| HPMC | 0.2 | 0.8 | 1.6 | 2.0 |
| Lidocaine 0.5 mg/ml | 3.8 | 3.2 | 2.4 | 2.0 |
| Final concentration of HPMC (mg/ml) | | | | |
| | 2.5 | 10 | 20 | 25 |
| Fluid viscosity | Liquid | Liquid | Liquid | Sligthly viscous |
| Osmolarity (mOsm/kg) | Not tested | Not tested | 329 | 325 |

EXAMPLE 6

A pertubation solution (50 ml, Table 3) containing glucose and albumin was prepared as follows.

Under aseptic conditions, NaCl (425 mg), $CaCl_2 \cdot H_2O$ (16.5 mg), lidocaine (25 mg) and glucose (1.25 g) were dissolved in 35 ml WFI in a glass beaker. The solution was heated to about 40° C. Albumin (1 ml of a 50 mg/ml solution of HSA) was added and the combined solutions swirled until completely mixed. The resulting clear solution was the sterilized by passing it through a 0.4 micron filter. Then 10 ml of sterile hyaluronic acid stock solution (gel) was aseptically added while preventing it from adhering to the vessels walls. The solution was gently swirled at 40° C. When the hyaluronic stock solution (gel) had fully dissolved in the lidocaine solution the pH was adjusted to 7.0 with sterile 1 M NaOH and the solution diluted with WFI to 50 ml. Osmolarity was measured and determined to be 295 mOsm/kg. The solution was aliquoted to 5 vials each containing 10 ml. The vials were cooled and stored refrigerated at from 4° C. to 8° C. Prior to use the vials were brought to room temperature.

TABLE 3

Hyaluronic acid-containing pertubation composition

| | (mg/50 ml) | (mg/ml per vial) |
|---|---|---|
| NaCl | 425 | 8.5 |
| KCl | 15 | 0.3 |
| $CaCl_2 \cdot H_2O$ | 16.5 | 0.33 |
| Lidocaine | 25 | 0.5 |
| Glucose | 1250 | 25 |
| Albumin | 50 | 1 |
| Hyaluronic acid | 400 | 8 |

EXAMPLE 7

Comparison of the composition of the invention with a corresponding prior art composition lacking albumin in a murine surgically-induced homologous endometriosis model.

The objective of the study was to assess the efficacy in improving fertility of the composition of the invention and a corresponding prior art composition lacking albumin ("prior art composition") in an endometrial auto-transplantation model in female C57BL/mice. The composition of the invention of Table 4 was used in the study.

TABLE 4

Composition of the invention used in the study

| Component | Amount (mg/ml) |
|---|---|
| Sodium chloride | 7.8 |
| Potassium chloride | 0.3 |
| Calcium chloride dihydrate | 0.33 |
| Lidocaine hydrochloride | 0.5 |
| Albumin | 1.0 |
| Hyaluronic acid | 1.0 |
| Sodium hydroxide | q.s., pH 7.0 |
| Water for injection | ad 1.0 ml |

Procedure. The study included four groups of n=5 female C57BL mice. Three groups were subjected to unilateral uterine horn resection and auto-transplantation of the endometriotic tissue adjacent to the arterial cascade of the intestinal mesentery while one group was subjected to unilateral uterine horn rejection only and served as sham-control. The female animals' estrous cycle was synchronized prior and following the surgical procedure and the reception potential assessed visually. Fertility of all females was assessed by mating success and subsequent litter size determination performed 6-7 weeks post-surgical procedure. Treatment was carried out by once daily repeated intraperitoneal injections for three successive days of the composition of the invention and the prior art composition to two of the endometrial auto-transplantation groups just prior to mating. The composition was administered at a dose per injection of 20 ml/kg body weight, that is, a dose of 10 mg of lidocaine/kg body weight. The other two groups were injected with a buffer control solution under identical experimental conditions and served as control groups. Animals were clinically observed for a duration of up to 10 weeks. No treatment mortalities were noted.

Results. Females from the group treated with the composition of the invention exhibited higher body weight gain than of the other groups. The difference was even higher when taking into account only the animals in which a copulatory plug was observed and/or suspected as pregnant during the rise in body weight. The results are shown in Table 4.

TABLE 4

Pregnancy efficacy of the composition of the invention in a C57BL mouse model

| Operation (n) | Composition | Pregnant animals (no/%) | Litter size per animal/total | Litter per pregnant animal (mean) | Litter per group (mean) |
|---|---|---|---|---|---|
| Endometriosis-induced (5) | Invention | 3 (60%) | 5, 3, 4 (12) | 4.0 | 2.4 |
| Endometriosis-induced (5) | Prior art | 2 (40%) | 3, 2 (5) | 2.5 | 1.0 |
| Endometriosis-induced (5) | Placebo | 1 (20%) | 3 (2) | 3.0 | 0.6 |
| Sham-operated control (5) | Placebo | 2 (40%) | 5, 6 (11) | 5.5 | 2.2 |

It is evident that the composition of the invention has substantially higher efficacy than the prior art composition, both being superior to placebo. The composition of the invention is even at least equivalent with placebo in the sham-operated control. The composition of the invention thus is capable of restoring fertility to normal levels in the presence of endometriosis.

The invention claimed is:

1. Pharmaceutical composition for treating infertility in a female subject, comprising:
    0.1 mg/mL to 2.5 mg/mL local anesthetic of amide type selected from the group consisting of articaine, bupivacaine, cinchocaine, etidocaine, levobupivacaine, lidocaine, mepivacaine, oxetacine, prilocaine, ropivacaine, tolycaine, and trimecaine,
    0.1 mg/mL to 20.0 mg/mL human albumin, wherein the human albumin is recombinant human albumin;
    viscosity controlling agent selected from the group consisting of recombinant hyaluronic acid and combination of recombinant hyaluronic acid and water-soluble cellulose ether; and water optionally comprising one or more ions selected from the group consisting of sodium, potassium, magnesium, calcium, acetate, chloride, and sulfate,
    wherein the composition is a perturbation solution adapted for perturbation.

2. The composition of claim 1, additionally comprising citrate, glucose and/or amino acid.

3. The composition of claim 2, comprising from 0.1 mM/L to 5.0 mM/L of citrate.

4. The composition of claim 2, comprising up to about 5 mg/ml of glucose.

5. The composition of claim 1, wherein the local anesthetic is in form of a pharmaceutically acceptable salt thereof.

6. The composition of claim 5, wherein the pharmaceutically acceptable salt is selected from hydrochloride, hydrobromide, and sulfate.

7. The composition of claim 1, wherein the local anesthetic is lidocaine or lidocaine hydrochloride.

8. The composition of claim 1, comprising from 0.02 mg/ml to 5.0 mg/ml of hyaluronic acid.

9. The composition of claim 1, wherein the cellulose ether is hydroxypropyl-methyl cellulose (HPMC).

10. A method for perturbation of the fallopian tubes of a female subject, comprising providing the pharmaceutical composition of claim 1; and administering a pharmacologically efficient amount of the composition by perturbation of the fallopian tubes of the female subject.

11. The composition of claim 1, wherein the human albumin is of recombinant origin and wherein the composition is free from macromolecules of animal or human origin.

12. The composition of claim 1, wherein the composition comprises:
- 0.3 to 1.5 mg/mL local anesthetic of amide type selected from the group consisting of articaine, bupivacaine, cinchocaine, etidocaine, levobupivacaine, lidocaine, mepivacaine, oxetacine, prilocaine, ropivacaine, tolycaine, and trimecaine;
- 0.5 to 10 mg/mL human albumin, wherein the human albumin is recombinant human albumin;
- viscosity controlling agent selected from the group consisting of recombinant hyaluronic acid and combination of recombinant hyaluronic acid and water-soluble cellulose ether; and
- water optionally comprising one or more ions selected from the group consisting of sodium, potassium, magnesium, calcium, acetate, chloride, and sulfate.

13. The composition of claim 12, wherein the composition comprises 0.02 mg/ml to 5 mg/ml recombinant hyaluronic acid.

14. A method of treating infertility in a female subject, comprising providing the pharmaceutical composition of claim 1; and administering a pharmacologically efficient amount of the composition to the abdominopelvic cavity of the female subject.

15. The method of claim 14, wherein said female subject has been diagnosed with unexplained infertility.

16. The method of claim 14, wherein said female subject has been diagnosed with endometriosis.

17. The method of claim 14, wherein administration is by perturbation of the fallopian tubes.

18. The method of claim 14, wherein administration is by infusion into the peritoneal cavity by means of a catheter.

19. The method of claim 14, wherein administration is by injection into the peritoneal cavity by means of a syringe.

20. The method of claim 14, wherein administration is by surgical deposition in the abdominal cavity.

21. The method of claim 14, wherein administration is by transdermal absorption via the abdominal wall.

22. Pharmaceutical composition according to claim 1, in dry powderous form for reconstitution with water, wherein said one or more ions selected from the group consisting of sodium, potassium, magnesium, calcium, acetate, chloride, and sulfate form part of the dry powderous form or of said water for reconstitution.

23. The composition of claim 22, wherein the dry powderous composition is in the form of a cryoprecipitate.

24. Sustained-release composition for treating infertility in a female subject, comprising:
- 0.1 mg/mL to 2.5 mg/mL local anesthetic of amide type selected from the group consisting of articaine, bupivacaine, cinchocaine, etidocaine, levobupivacaine, lidocaine, mepivacaine, oxetacine, prilocaine, ropivacaine, tolycaine, and trimecaine,
- 0.1 mg/mL to 20.0 mg/mL human albumin, wherein the human albumin is recombinant human albumin; and
- viscosity controlling agent selected from the group consisting of recombinant hyaluronic acid and combination of recombinant hyaluronic acid and water-soluble cellulose ether, wherein the composition is incorporated into a biodegradable porous polymer microparticle or a microparticle comprising a biodegradable polymer shell.

25. The composition of claim 24, wherein the porous polymer or the polymer shell comprises a biodegradable polymer selected from poly-lactide, poly-glycolide, and poly(lactide-co-glycolide).

26. Pharmaceutical composition for treating infertility in a female subject, consisting essentially of:
- 0.1 mg/mL to 2.5 mg/mL local anesthetic of amide type selected from the group consisting of articaine, bupivacaine, cinchocaine, etidocaine, levobupivacaine, lidocaine, mepivacaine, oxetacine, prilocaine, ropivacaine, tolycaine, and trimecaine,
- 0.1 mg/mL to 20.0 mg/mL human albumin, wherein the human albumin is recombinant human albumin;
- viscosity controlling agent selected from the group consisting of recombinant hyaluronic acid and combination of recombinant hyaluronic acid and water-soluble cellulose ether; and
- water optionally comprising one or more ions selected from the group consisting of sodium, potassium, magnesium, calcium, acetate, chloride, and sulfate,
- wherein the composition is a perturbation solution adapted for perturbation.

27. The composition of claim 26, wherein the human albumin is of recombinant origin and wherein the composition is free from macromolecules of animal or human origin.

28. The composition of claim 26, wherein the composition consists essentially of:
- 0.3 to 1.5 mg/mL local anesthetic of amide type selected from the group consisting of articaine, bupivacaine, cinchocaine, etidocaine, levobupivacaine, lidocaine, mepivacaine, oxetacine, prilocaine, ropivacaine, tolycaine, and trimecaine;
- 0.5 to 10 mg/mL human albumin, wherein the human albumin is recombinant human albumin;
- viscosity controlling agent selected from the group consisting of recombinant hyaluronic acid and combination of recombinant hyaluronic acid and water-soluble cellulose ether; and
- water optionally comprising one or more ions selected from the group consisting of sodium, potassium, magnesium, calcium, acetate, chloride, and sulfate.

29. The composition of claim 28, wherein the recombinant hyaluronic acid is included in an amount of 0.02 mg/ml to 5 mg/ml.

* * * * *